United States Patent
Choi et al.

(10) Patent No.: US 11,008,274 B2
(45) Date of Patent: May 18, 2021

(54) METHOD FOR MANUFACTURING DIMETHYLOLBUTANAL AND METHOD FOR MANUFACTURING TRIMETHYLOLPROPANE USING SAME

(71) Applicant: LG CHEM, LTD., Seoul (KR)

(72) Inventors: Min Ji Choi, Daejeon (KR); Sungshik Eom, Daejeon (KR); Dawon Jung, Daejeon (KR); Tae Yun Kim, Daejeon (KR); Dong Hyun Ko, Daejeon (KR); Mi Young Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 17/041,259

(22) PCT Filed: Jul. 10, 2019

(86) PCT No.: PCT/KR2019/008471
§ 371 (c)(1),
(2) Date: Sep. 24, 2020

(87) PCT Pub. No.: WO2020/085613
PCT Pub. Date: Apr. 30, 2020

(65) Prior Publication Data
US 2021/0009493 A1 Jan. 14, 2021

(30) Foreign Application Priority Data
Oct. 22, 2018 (KR) .................. 10-2018-0125970

(51) Int. Cl.
*C07C 45/64* (2006.01)
*C07C 29/00* (2006.01)
*C07C 29/153* (2006.01)

(52) U.S. Cl.
CPC ............ *C07C 45/64* (2013.01); *C07C 29/153* (2013.01)

(58) Field of Classification Search
CPC ...... C07C 45/64; C07C 29/141; C07C 29/151
See application file for complete search history.

(56) References Cited

U.S. PATENT DOCUMENTS

| | | | |
|---|---|---|---|
| 5,763,690 A | 6/1998 | Salek et al. | |
| 6,080,896 A * | 6/2000 | Ninomiya | C07C 29/38 568/853 |
| 6,593,502 B2 * | 7/2003 | Salmi | C07C 29/141 568/852 |
| 2002/0077502 A1 | 6/2002 | Dobert et al. | |
| 2002/0107417 A1 | 8/2002 | Watanabe et al. | |
| 2008/0167506 A1 | 7/2008 | Sirch et al. | |
| 2015/0368171 A1 | 12/2015 | Hampton, Jr. et al. | |
| 2017/0349512 A1 | 12/2017 | Eom et al. | |
| 2020/0369588 A1 * | 11/2020 | Eom | C07C 47/19 |

FOREIGN PATENT DOCUMENTS

| | | |
|---|---|---|
| JP | 2002193854 A | 7/2002 |
| JP | 2002226426 A | 8/2002 |
| KR | 20090098917 A | 9/2009 |
| KR | 20110071898 A | 6/2011 |
| KR | 20150009226 A | 1/2015 |
| KR | 20150113121 A | 10/2015 |
| KR | 20150118808 A | 10/2015 |
| KR | 20170029311 A | 3/2017 |
| KR | 20180047255 A | 5/2018 |
| KR | 20180047257 A | 5/2018 |

* cited by examiner

*Primary Examiner* — Sikarl A Witherspoon
(74) *Attorney, Agent, or Firm* — Dentons US LLP

(57) ABSTRACT

A method for preparing dimethylolbutanal including performing an aldol reaction of n-butyraldehyde (n-BAL) and paraformaldehyde (PFA) in the presence of water and an alkylamine catalyst, in which a weight ratio of the paraformaldehyde:water is 1:0.35 to 1:0.85.

10 Claims, No Drawings

METHOD FOR MANUFACTURING DIMETHYLOLBUTANAL AND METHOD FOR MANUFACTURING TRIMETHYLOLPROPANE USING SAME

CROSS-REFERENCE TO RELATED APPLICATIONS

This application is a national stage of international Application No. PCT/KR2019/008471 filed on Jul. 10, 2019, and claims priority to and the benefit of Korean Patent Application No. 10-2018-0125970 filed in the Korean Intellectual Property Office on Oct. 22, 2018, the entire contents of which are incorporated herein by reference in their entirety as if fully set forth herein.

TECHNICAL FIELD

The present application relates to a method for preparing dimethylolbutanal and a method for preparing trimethylolpropane using the same.

BACKGROUND

Trimethylolpropane (TMP) may be prepared by various methods, including a method of preparing trimethylolpropane via a Cannizzaro reaction using n-butylaldehyde (n-BAL) and formaldehyde (FA) in the presence of an alkalimetal (usually, NaOH) catalyst as described below:

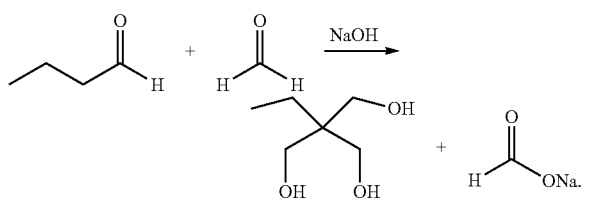

In the TMP preparation method using a Cannizzaro reaction, usually a commercialization process for preparing TMP, 1 mol of metal formate (formate salt) per 1 mol of TMP is produced as a by-product, so that the TMP preparation method is not efficient.

Trimethylolpropane is a white crystalline substance at room temperature, and is widely used as a raw material in various fields such as alkyd resins, saturated polyesters, synthetic lubricants, polyurethane resins, and plasticizers. Therefore, studies for an economical method for producing trimethylolpropane, which is an industrially important raw material, have been continuously conducted.

SUMMARY

The present application provides a method for preparing dimethylolbutanal and a method for preparing trimethylolpropane using the same.

An exemplary embodiment of the present application provides a method for preparing dimethylolbutanal, the method comprising: subjecting n-butylaldehyde (n-BAL) and paraformaldehyde (PFA) to an aldol reaction in the presence of water and an alkylamine catalyst, in which a weight ratio of the paraformaldehyde:the water is 1:(0.35 to 0.85).

Further, another exemplary embodiment of the present application provides a method for preparing trimethylolpropane, the method comprising:

preparing dimethylolbutanal by the method for preparing dimethylolbutanal; and preparing trimethylolpropane (TMP) by performing a hydrogenation reaction in the presence of a metal catalyst.

The method for preparing dimethylolbutanal according to an exemplary embodiment of the present application may adjust the content of water by applying paraformaldehyde instead of formalin, which is used in the related art. Accordingly, it is possible to effectively increase a process efficiency by increasing the yield of an active ingredient and the selectivity of dimethylolbutanal (DMB).

Further, trimethylolpropane may be obtained at a high yield using the dimethylolbutanal prepared according to an exemplary embodiment of the present application as a raw material for a hydrogenation reaction.

DETAILED DESCRIPTION

Hereinafter, the present application will be described in more detail.

In the present application, the "extraction efficiency" is defined as a ratio of the weight of an extracted substance comprised in an extraction solvent obtained after the extraction to the weight of the target substance comprised in extracted raw material to be introduced into the reaction.

Further, in the present application, the 'yield' is defined as a value obtained by dividing the amount of product actually produced in a reaction by a maximum production amount that may be theoretically expected.

In addition, in the present application, the 'conversion (%)' refers to a rate at which a reactant is converted into a product, and for example, the FA conversion may be defined by the following equation:

Conversion (%)=[(the number of moles of FA reacted)/(the number of moles of FA supplied)]×100.

Furthermore, in the present application, the 'selectivity (%)' is defined as a value obtained by dividing the change amount of DMB by the change amount of FA. For example, the DMB selectivity may be represented by the following equation:

Selectivity (%)=[(the number of moles of DMB produced)/(the number of moles of FA reacted)]×100.

In the case of the Cannizzaro method of preparing TMP, a formate salt is produced as a byproduct while TMP is produced from n-BAL. However, in the preparation method of trimethylolpropane according to an exemplary embodiment of the present application, after the aldol reaction, DMB is separated by an extraction method, and then TMP is produced via the hydrogenation process, reducing the production of the byproduct.

As DMB and a part of TMP are formed after the aldol reaction, small amounts of salts are produced, and the reactivity and stability during the subsequent hydrogenation reaction deteriorate unless the salts are removed. When trimethylolpropane is produced by the hydrogenation reaction, it is necessary to effectively separate dimethylolbutanal (DMB) as a precursor material of trimethylolpropane after the first step of the aldol reaction.

Further, when formalin is used in the aldol reaction, about 42% of formaldehyde is dissolved in about 56% of water, and the other part is composed of MeOH. When the formalin is used, about 40% of moisture remains in the aldol condensation reactant, and this causes the extraction efficiency to be reduced in an extraction process, which is a separation process.

Accordingly, the present application is intended to reduce the content of moisture comprised in the aldol condensation reactant and increase the extraction efficiency.

The method for preparing dimethylolbutanal according to an exemplary embodiment of the present application comprises a process of subjecting n-butylaldehyde (n-BAL) and paraformaldehyde (PFA) to an aldol reaction in the presence of water and an alkylamine catalyst, in which a weight ratio of the paraformaldehyde:the water is 1:(0.35 to 0.85).

In an exemplary embodiment of the present application, a reactor in which the process of subjecting n-butylaldehyde (n-BAL) and paraformaldehyde (PFA) to the aldol reaction is performed is not particularly limited as long as the reactor may be used in the aldol reaction. For example, the reactor may be a jacket type reactor, but is not limited thereto.

In an exemplary embodiment of the present application, in the process of subjecting n-butylaldehyde (n-BAL) and paraformaldehyde (PFA) to the aldol reaction, n-butylaldehyde, paraformaldehyde, water, and an alkylamine catalyst may be simultaneously introduced into the reactor, or a part of them may also be introduced into the reactor before the other parts. For example, in order to improve the reaction efficiency to a greater extent, it is preferred that n-butylaldehyde, paraformaldehyde, and water are first introduced into the reactor, and then the alkylamine catalyst is slowly introduced into the reactor. Further, it is possible to introduce the n-butylaldehyde, the paraformaldehyde, the water, and the alkylamine catalyst into the reactor, and then stir the resulting mixture. Further, it is possible to introduce the n-butylaldehyde, the paraformaldehyde, and the alkylamine catalyst into a first reactor, and then stir the resulting mixture simultaneously with the reaction. That is, the reaction and the stirring may be simultaneously performed. The stirring speed for the mixture may be 150 rpm to 350 rpm, and more preferably 200 rpm to 300 rpm.

In an exemplary embodiment of the present application, a weight ratio of the paraformaldehyde: the water may be 1:(0.35 to 0.85), and may be 1:(0.38 to 0.8). When the weight ratio of the water is less than 0.35, PFA is slowly dissolved in water, so that the reaction rate slows down. Accordingly, the conversion and yield are decreased, and when distilled water is rarely present, the reaction does not occur. Further, when the weight ratio of the water is more than 0.85, there is no big difference between the use of 42% formaldehyde in the related art (moisture in the reactant: about 40%) and the content of moisture, and the conversion is high, but the selectivity of DMB is decreased. In addition, when the weight ratio of the water is more than 0.85, the content of moisture in the reaction product is high and the content of DMB is relatively small, so that the amount of solvent used has to be increased to show the same extraction efficiency during the extraction process after the aldol reaction.

In an exemplary embodiment of the present application, a molar ratio of the n-butylaldehyde: the paraformaldehyde may be 1:(2.5 to 4), and may be 1:(2.8 to 3.7). When the content of formaldehyde is less than 2.5 mol based on 1 mol of the n-butylaldehyde, the reaction yield may rapidly decrease, and when the content is more than 4 mol, the amount of formaldehyde to be recovered after the reaction may rapidly increase as compared to the increase in the width of the reaction yield, so that the economic feasibility may deteriorate.

In an exemplary embodiment of the present application, a molar ratio of the n-butylaldehyde: the alkylamine catalyst may be 1:(0.1 to 0.3), and may be 1:(0.15 to 0.25). When the content of the alkylamine catalyst is less than 0.1 mol based on 1 mol of the n-butylaldehyde, the reaction rate slows down, so that the reaction time may increase, and when the content is more than 0.3 mol, economic feasibility may deteriorate because the catalyst is used in a large amount.

In an exemplary embodiment of the present application, the process of subjecting n-butylaldehyde (n-BAL) and paraformaldehyde (PFA) to the aldol reaction may be performed at a temperature of 20° C. to 50° C., and at a temperature of 30° C. to 40° C. When the temperature of the process of subjecting n-butylaldehyde (n-BAL) and paraformaldehyde (PFA) to the aldol reaction is less than 20° C., the conversion decreases and the reaction rate slows down, so that there may occur a problem in that the total reaction time may increase. In addition, when the temperature of the process of subjecting n-butylaldehyde (n-BAL) and paraformaldehyde (PFA) to the aldol reaction is more than 50° C., a side reaction increases, and the yield may decrease.

In an exemplary embodiment of the present application, the alkylamine catalyst may comprise an alkylamine having 3 to 20 carbon atoms. More specifically, the alkylamine catalyst may comprise one or more of trimethylamine, triethylamine (TEA), tripropylamine, and diisopropylethylamine, and preferably triethylamine.

In an exemplary embodiment of the present application, after the process of subjecting n-butylaldehyde (n-BAL) and paraformaldehyde (PFA) to the aldol reaction, it is possible to additionally perform an extraction process using an alcohol solvent. The alcohol solvent may be an alcohol solvent having 2 to 10 carbon atoms. Specifically, the alcohol solvent may be an alcohol solvent having 6 to 8 carbon atoms, and may be preferably an alcohol solvent having 8 carbon atoms. In an exemplary embodiment of the present specification, the alcohol solvent may be 2-ethylhexanol (2-EH).

In an exemplary embodiment of the present application, a weight ratio of an aldol product produced after the process of subjecting n-butylaldehyde (n-BAL) and paraformaldehyde (PFA) to the aldol reaction: the alcohol solvent may be 1:(0.3 to 1.5), and may be 1:(0.5 to 1.3). When the weight ratio of the alcohol solvent is less than 0.3, the extraction efficiency may decrease. When the weight ratio is more than 1.5, the extraction efficiency may increase, but the cost of treating the used solvent increases because the amount of solvent used is increased, so that the weight ratios out of the weight ratio range are not preferred.

In an exemplary embodiment of the present application, the extraction temperature in the extracting of the product is preferably 25° C. to 90° C., and specifically, the extraction temperature is preferably 30° C. to 70° C. When the extraction temperature is satisfied, the extraction yield may be increased.

The method for preparing trimethylolpropane according to an exemplary embodiment of the present application comprises: preparing dimethylolbutanal according to the method for preparing dimethylolbutanal; and preparing trimethylolpropane (TMP) by performing a hydrogenation reaction in the presence of a metal catalyst.

In an exemplary embodiment of the present application, the metal catalyst may be a copper-based metal catalyst. The copper-based metal catalyst is not limited as long as the copper-based metal catalyst is used for the hydrogenation reaction.

In an exemplary embodiment of the present application, a reactor used in the method for preparing trimethylolpropane may be a batch type hydrogenation reactor, but is not limited thereto.

In an exemplary embodiment of the present application, the reaction temperature of the hydrogenation reaction may be 80° C. to 150° C., preferably 100° C. to 140° C., and more preferably 110° C. to 130° C. A reaction pressure of the hydrogenation reaction may be 20 bar to 70 bar. Preferably, the reaction pressure may be 25 bar to 50 bar. When the reaction temperature and reaction pressure of the hydrogenation reaction satisfy the above-described ranges, trimethylolpropane may be prepared at a high yield.

In an exemplary embodiment of the present application, a molar ratio of hydrogen ($H_2$) based on 1 mol of dimethylolbutanal during the hydrogenation reaction may be 1 to 3, preferably 1 to 2.

In an exemplary embodiment of the present application, the method of preparing the trimethylolpropane may produce trimethylolpropane with a yield of 70% or more, and with a yield of 75% or more.

In an exemplary embodiment of the present application, the method for preparing trimethylolpropane may further comprise, after trimethylolpropane is prepared by the hydrogenation reaction, purifying the prepared trimethylolpropane.

Hereinafter, the present application will be described in detail with reference to Examples for specifically describing the present application. However, the Examples according to the present application may be modified in various forms, and the scope of the present application is not limited to the Examples described in detail below. The Examples of the present application are provided for more completely explaining the present application to the person with ordinary skill in the art.

EXAMPLES

Example 1

After 120 g of n-butylaldehyde (n-BAL) and 180 g of paraformaldehyde (PFA) were introduced into a 1 L-reactor in which the temperature could be adjusted, distilled water was introduced thereto and the resulting mixture was stirred. In this case, distilled water was introduced thereinto in an mount corresponding to 0.4 times the weight of PFA. The reaction was started by slowly adding 25 g of a base catalyst TEA dropwise thereto. The reaction was performed for 6 hours while adjusting the temperature at 35° C. The molar ratio of the n-BAL: the PFA was 1:3.6, and the molar ratio of the n-BAL: the TEA was 1:0.15.

Example 2

An experiment was performed in the same manner as in Example 1, except that the distilled water was introduced thereinto in an amount corresponding to 0.46 times the weight of PFA in Example 1.

Example 3

An experiment was performed in the same manner as in Example 1, except that the distilled water was introduced thereinto in an amount corresponding to 0.78 times the weight of PFA in Example 1.

Example 4

200 g of the aldol reactant in Example 2 was introduced into a separatory funnel, and then 2-ethyl hexanol was introduced thereinto at an amount corresponding to the weight of the reactant. After shaking by hand for 5 minutes, the reactant was left to stand for 30 minutes to separate an extract and a raffinate.

Example 5

An experiment was performed in the same manner as in Example 4, except that 2-ethyl hexanol was introduced thereinto at an amount corresponding to 0.8 times the weight of the reactant during the extraction in Example 4.

Example 6

An experiment was performed in the same manner as in Example 4, except that 2-ethyl hexanol was introduced thereinto at an amount corresponding to 0.6 times the weight of the reactant during the extraction in Example 4.

Comparative Example 1

After 120 g of n-BAL and 430 g of formalin ($H_2O$/FA=1.3) were introduced into a 1 L-reactor in which the temperature could be adjusted, the reaction was started by slowly adding 25 g of a base catalyst TEA dropwise thereto. The reaction was performed for 3 hours while adjusting the temperature to be at 35° C. The molar ratio of the n-BAL: the FA was 1:3.6, and the molar ratio of the n-BAL: the TEA was 1:0.15.

Comparative Example 2

After 120 g of n-BAL and 180 g of PFA were introduced into a 1 L-reactor in which the temperature could be adjusted, distilled water was introduced thereto and the resulting mixture was stirred. In this case, distilled water was introduced thereinto in an amount corresponding to 0.01 times the weight of PFA. The reaction was started by slowly adding 25 g of a base catalyst TEA dropwise thereto. The reaction was performed for 6 hours while adjusting the temperature to be at 35° C. The molar ratio of the n-BAL: the PFA was 1:3.6, and the molar ratio of the n-BAL: the TEA was 1:0.15.

Comparative Example 3

An experiment was performed in the same manner as in Comparative Example 2, except that the distilled water was introduced thereinto in an amount corresponding to 0.2 times the weight of PFA in Comparative Example 2.

Comparative Example 4

200 g of the aldol reactant in Comparative Example 1 was introduced into a separatory funnel, and then 2-ethyl hexanol was introduced thereinto at an amount corresponding to the weight of the reactant. After shaking by hand for 5 minutes, the reactant was left to stand for 30 minutes to separate an extract and a raffinate.

Comparative Example 5

An experiment was performed in the same manner as in Comparative Example 4, except that 2-ethyl hexanol was introduced thereinto at an amount corresponding to twice the weight of the reactant during the extraction in Comparative Example 4.

Comparative Example 6

An experiment was performed in the same manner as in Comparative Example 4, except that 2-ethyl hexanol was introduced thereinto at an amount corresponding to 6 times the weight of the reactant during the extraction in Comparative Example 4.

Experimental Example 1

By performing GC analysis, FA analysis, and moisture analysis of the reactants produced after the aldol reaction process in Examples 1 to 3 and Comparative Examples 1 to 3, the composition thereof was confirmed, and the conversion, yield, selectivity, and the like were calculated. The results are shown in the following Table 1:

TABLE 1

| | Conversion (%) | Yield (%) of active ingredient | Selectivity (%) of DMB |
|---|---|---|---|
| Example 1 | 99.9 | 87.0 | 76.0 |
| Example 2 | 99.9 | 89.7 | 80.1 |
| Example 3 | 99.9 | 89.9 | 74.2 |
| Comparative Example 1 | 99.9 | 90.0 | 69.7 |
| Comparative Example 2 | — | — | — |
| Comparative Example 3 | 99.9 | 77.3 | 71.1 |

In Comparative Example 2, the reaction was not performed.

Experimental Example 2

After the extraction process in Examples 4 to 6 and Comparative Examples 4 to 6, GC analysis, FA analysis, and moisture analysis were performed to confirm the composition of each layer and calculate the extraction yields. The results are shown in the following Table 2:

TABLE 2

| | Weight ratio of 2-EH/reactant | Extraction yield (%) of DMB |
|---|---|---|
| Example 4 | 1 | 88 |
| Example 5 | 0.8 | 89 |
| Example 6 | 0.6 | 87 |
| Comparative Example 4 | 1 | 74 |
| Comparative Example 5 | 2 | 82 |
| Comparative Example 6 | 6 | 86 |

As shown by the results, the method for preparing dimethylolbutanal according to an exemplary embodiment of the present application may adjust the content of water by applying paraformaldehyde instead of formalin, which is used in the related art, and accordingly, it is possible to effectively increase process efficiency by increasing the yield of an active ingredient and the selectivity of dimethylolbutanal (DMB).

Further, trimethylolpropane may be obtained at a high yield using the dimethylolbutanal prepared according to an exemplary embodiment of the present application as a raw material for a hydrogenation reaction.

The invention claimed is:

1. A method for preparing dimethylolbutanal, the method comprising:
    performing an aldol reaction of n-butylaldehyde (n-BAL) and paraformaldehyde (PFA) in the presence of water and an alkylamine catalyst,
    wherein a weight ratio of the paraformaldehyde:water is 1:0.35 to 1:0.85.

2. The method of claim 1, wherein a molar ratio of the n-butylaldehyde:paraformaldehyde is 1:2.5 to 1:4.

3. The method of claim 1, wherein a molar ratio of the n-butylaldehyde:alkylamine is 1:0.1 to 1:0.3.

4. The method of claim 1, wherein performing the aldol reaction of n-butylaldehyde (n-BAL) and paraformaldehyde (PFA) in the presence of water and an alkylamine catalyst comprises: a first step of introducing n-butylaldehyde, paraformaldehyde, and water into a reactor, and
    a second step of introducing the alkylamine catalyst into the reactor.

5. The method of claim 1, wherein the aldol reaction is performed at a temperature of 20° C. to 50° C.

6. The method of claim 1, wherein the alkylamine catalyst comprises one or more selected from trimethylamine, triethylamine, tripropylamine, and diisopropylethylamine.

7. The method of claim 1, further comprising performing an extraction process using an alcohol solvent after performing the aldol reaction.

8. The method of claim 7, wherein the alcohol solvent is 2-ethyl hexanol (2-EH).

9. The method of claim 7, wherein a weight ratio of a product of the aldol reaction:the alcohol solvent is 1:0.3 to 1:1.5.

10. A method for preparing trimethylolpropane, the method comprising:
    preparing dimethylolbutanal according to the method of claim 1; and
    performing a hydrogenation reaction of the dimethylolbutanal in the presence of a metal catalyst to obtain the trimethylolpropane (TMP).

* * * * *